United States Patent [19]
Takenishi et al.

[11] Patent Number: 6,017,742
[45] Date of Patent: Jan. 25, 2000

[54] IMMOBILIZATION OF BIOLOGICALLY ACTIVE SUBSTANCES ON A CARRIER CONTAINING A CARBODIIMIDE GROUP-CONTAINING POLYMER

[75] Inventors: Soichiro Takenishi; Osamu Suzuki; Yasuo Imashiro; Ikuo Takahashi; Naokazu Sasaki; Tomoaki Shoji; Hiroko Matsubayashi, all of Tokyo, Japan

[73] Assignee: Nisshinbo Industries, Inc., Tokyo, Japan

[21] Appl. No.: 09/009,541

[22] Filed: Jan. 20, 1998

Related U.S. Application Data

[63] Continuation of application No. 08/500,206, Jul. 10, 1995, abandoned.

[30] Foreign Application Priority Data

Jul. 20, 1994 [JP] Japan ..................................... 6-191035

[51] Int. Cl.⁷ ......................... C12N 11/08; G01N 33/545; C07K 17/08
[52] U.S. Cl. ......................... 435/180; 435/174; 435/177; 435/181; 436/524; 436/528; 436/531; 436/532; 530/811; 530/812; 530/815; 530/816
[58] Field of Search ..................................... 435/176, 177, 435/180, 171; 436/524, 528, 531, 532; 530/811, 812, 815, 816

[56] References Cited

U.S. PATENT DOCUMENTS

| | | | |
|---|---|---|---|
| 4,118,536 | 10/1978 | Beardsley et al. | 428/413 |
| 4,855,234 | 8/1989 | Hendrickson et al. | 435/181 |
| 5,079,326 | 1/1992 | Suzuki et al. | 528/53 |
| 5,373,080 | 12/1994 | Imashiro et al. | 528/67 |

OTHER PUBLICATIONS

Oskar Zaborsky; "Immobilized Enzymes"; CRC Press; 1973; pp. 26–27.

*Primary Examiner*—David M. Naff
*Attorney, Agent, or Firm*—Kubovcik & Kubovcik

[57] ABSTRACT

A material is provided for immobilization of biologically active substances which are reactive with a carbodiimide group. The material contains a carbodiimide group-containing polymer supported on a carrier such as a plastic, an inorganic polymer, a metal, a natural polymer or a ceramic. The carbodiimide group-containing polymer has 2 to 100 carbodiimide groups per molecule and a molecular weight of 1,000 to 100,000, and is prepared by carbodiimidization of an organic polyisocyanate in the presence of a catalyst. The polymer may be supported as a film on part or the whole area of the carrier. Biologically active substances that may be immobilized include enzymes, hormones, antibodies, antigens, heptenes, peptides, DNAs and RNAs.

6 Claims, No Drawings

SEQUENCE LISTING

<160> NUMBER OF SEQ ID NOS: 1

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: synthetic DNA sequence

<400> SEQUENCE: 1
gaggatcccc gggtaccgag ctcgaattc                                    29

IMMOBILIZATION OF BIOLOGICALLY ACTIVE SUBSTANCES ON A CARRIER CONTAINING A CARBODIIMIDE GROUP-CONTAINING POLYMER

This application is a continuation of application Ser. No. 08/500,206, filed Jul. 10, 1995, now abandoned.

BACKGROUND OF THE INVENTION

1. Field of the Invention

The present invention relates to a material for immobilization of biologically active substance, as well as to a method for immobilization of said substance using said material.

2. Description of the Prior Art

A biologically active substance (hereinafter referred to simply as "active substance", in some cases) such as protein, nucleic acid, oligopeptide, oligonucleotide or the like, immobilized on an insoluble material is useful because the immobilization enables the easy utilization of the activity of said substance. Examples of such utilization includes the industrial utilization of immobilized enzyme in the field of biochemistry or science, the immunological utilization of immobilized antibody or antigen, and the utilization of immobilized nucleic acid as diagnostic drug.

In this connection, various methods for immobilization of active substance were reported. For immobilization of, for example, an enzyme, there are methods such as the following.

(1) A method for immobilizing an enzyme on a material by chemical bonding using a crosslinking agent, a condensation agent or the like, for example, a diazo method, a peptide method, an alkylation method, a method using a crosslinking agent and a method using an Ugi reaction [Immobilized Enzyme, pp. 9–41 (1986), edited by Ichiro Chihata and published from Kodansha Scientific].

(2) A method for immobilizing an enzyme on a material by ionic bonding (Immobilized Enzyme, pp. 41–43).

(3) A method for immobilizing an enzyme on a material by physical adsorption (Immobilized Enzyme, pp. 43–45).

For immobilization of a nucleic acid, there are methods such as the following.

(1) A method for immobilizing a modification group-containing nucleic acid on a material by chemical bonding, for example, a method for bonding a nucleic acid having a thiol group at the 5' terminal, to a thiol group-containing bead-like material by disulfide bonding [P. J. R. Day, P. S. Flora, J. E. Fox, M. R. Walker, Biochem. J., Vol. 278, pp. 735–740 (1991)]. Other methods falling in this method (1) are described in, for example, Soren R. R., Mette R. L., Svend E. R., Anal. Biochem., Vol. 198, pp. 138–142 (1991); Jonathan N K., Joseph L. W., Joseph P. D., Rachel E. M., Mary C., Eugene L. B., Nucleic Acids Res., Vol. 15, pp. 2891–2909 (1987); Allan J. M., Jeffrey R. B., Terence W. P., Biochem J., Vol. 191, pp.276–279 (1990); and J. A. Running, M. S. Ureda, Biotechniques, Vol. 8, pp. 276–279 (1990).

(2) A method for immobilizing a nucleic acid on a material by physical adsorption, for example, a method for immobilizing a nucleic acid on a nitrocellulose or nylon film by physical adsorption using ultraviolet rays or heat (J. Sambrok, E. F. Fritsh, T. Maniatis, Molecular Cloning, Cold Spring Harbor Laboratory Press, Second Edition, pp. 2.109–2.113 and pp. 9.36–9.46) and a method for immobilizing a nucleic acid on a microplate by physical adsorption [G. C. N. Parry, A. D. B. Malcolm, Biochem. Soc. Trans., Vol. 17, pp. 230–231 (1989)].

It is pointed out that the above conventional methods have problems. For example, in the methods by chemical bonding, special reagents are necessary and some of them (e.g. azide, isocyanate and $NaBH_3CN$) are poisonous. Moreover, the procedure of immobilization is complicated as follows. For example, when immobilization is conducted via a peptide bond, it is necessary to introduce an amino group into either one of the active substance and the material and a carboxyl group into the other and these two kinds of groups introduced must be reacted with each other for immobilization by the use of a condensation agent.

Also in the methods by chemical bonding, the material used must have a functional group (for example, when glutaraldehyde is used as a crosslinking agent, the material and the active substance each must have an amino group), and a material allowing for immobilization must be selected carefully. Further, a substance having no active group is impossible to immobilize on a material. For example, a substance (e.g. a natural DNA, or a synthetic DNA having no modification group) having only a functional group of low reactivity (e.g. terminal phosphoric acid group or terminal hydroxyl group) is difficult to immobilize by the method of chemical bonding.

Meanwhile in the methods by physical adsorption, there are problems such as (1) the amount of active substance immobilized varies depending upon the adsorbability of material, (2) the active substance adsorbed is desorbed easily, (3) when the active substance has a low molecular weight (oligomer), its interaction with the material is weak, making the adsorption difficult. Further, when a nucleic acid is immobilized on a nylon or nitrocellulose film by adsorption, both the adsorption density and the bonding strength are high but the film has insufficient strength and is broken easily, requiring thorough care in handling.

SUMMARY OF THE INVENTION

The objects of the present invention are to provide a material for immobilization of an active substance, which is free from the problems of the prior art, which can immobilize an active substance easily and which is easy to handle, and a method for immobilization of said substance using said material.

According to the present invention, there is provided a material for immobilization of biologically active substance, which comprises a carrier and a carbodiimide group-containing polymer supported thereon.

According to the present invention, there is also provided a method for immobilization of a biologically active substance, which comprises contacting a biologically active substance reactive with a carbodiimide group with a material for immobilization of said substance comprising a carrier and a carbodiimide group-containing polymer supported thereon.

Low-molecular weight carbodiimide derivatives such as dicyclohexylcarbodiimide, di-p-toluoylcarbodiimide and the like have been used widely as a hydration and condensation agent in the synthesis of ester, peptide or the like. These carbodiimide derivatives each form an adduct with a carboxylic acid easily as shown in the following reaction formulas, and each adduct gives rise to a condensation reaction with an alcohol, an amine, a carboxylic acid or the like while liberating an urea derivative, to form a corresponding ester, amide or acid anhydride. It was therefore considered to use such low-molecular weight carbodiimide derivatives for immobilization of an active substance.

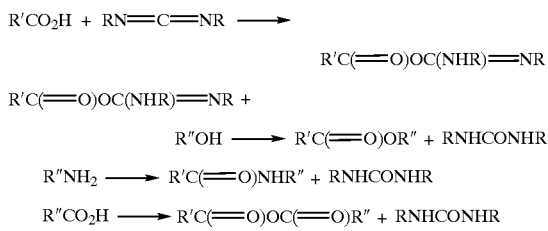

These low-molecular weight carbodiimide derivatives were developed for use as a condensation agent and are soluble in solvents. They are easily eliminated when supported on a material and their use in a supported form is not practical. Hence, the present inventors focused on a high-molecular weight carbodiimide compound having carbodiimide groups in the molecule and made a study on this compound. As a result, the present inventors found out that such a carbodiimide compound has not only a reactivity with an active substance but also good adhesion to various materials. The finding has led to the completion of the present invention.

DETAILED DESCRIPTION OF THE INVENTION

The present invention is hereinafter described in detail.

The carrier used in the present invention acts as a carrier for immobilizing an active substance thereon. Basically, it is insoluble in water or solvents and solid at normal temperature or in its vicinity (0–100° C.). Preferable examples thereof are a plastic, a glass, a metal, an inorganic polymer, a natural polymer and a ceramic.

Specific examples of the carrier are as follows.

Plastic: polyethylene, polystyrene, polycarbonate, polypropylene, polyamide, phenolic resin, epoxy resin, polycarbodiimide resin, polyvinyl chloride, polyvinylidene fluoride, polyethylene fluoride, polyimide, acrylic resin or the like.

Inorganic polymer: glass, rock crystal, carbon, silicagel, graphite or the like.

Metal: gold, platinum, silver, copper, iron, aluminum, magnet, paramagnet, apatite or the like, which are all solid at normal temperature.

Natural polymer: cellulose, cellulose derivative, chitin, chitosan, alginic acid or the like.

Ceramic: alumina, silica, silicon carbide, silicon nitride, boron carbide or the like.

The shape of the carrier includes, for example, a film, a board, particles and molded materials such as beads, strip, multiwell plate, well of multiwell plate, unit of separable multiwell plate, stripwell of multiwell plate, tube, mesh, foamed plastic, membrane, paper, needle, fiber, plate, slide, cell incubator and the like. Needless to say, the size of the carrier has no particular restriction.

The carbodiimide group-containing polymer (hereinafter referred to simply as "carbodiimide compound", in some cases) used in the present invention includes, for example, those polycarbodiimides which can be produced, for example, by a process disclosed in Japanese Patent Application Kokai (Laid-Open) No. 61599/1976, a process by M. Alberino et al. described in J. Appl. Polym. Sci., Vol. 21, p. 190 (1990) or a process disclosed in Japanese Patent Application Kokai (Laid-Open) No. 292316/1990. The above polycarbodiimides can be produced from an organic polyisocyanate compound in the presence of a catalyst which promotes the carbodiimidization of said isocyanate.

The organic polyisocyanate compound can be exemplified by 2,4-tolylene diisocyanate, 2,6-tolylene diisocyanate, a mixture of 2,4-tolylene diisocyanate and 2,6-tolylene diisocyanate, crude tolylene diisocyanate, crude methylene diphenyl diisocyanate, 4,4',4"-triphenylmethylene triisocyanate, xylene diisocyanate, hexamethylene-1,6-diisocyanate, lysine diisocyanate, hydrogenated methylene diphenyl diisocyanate, m-phenyl diisocyanate, naphthylene-1,5-diisocyanate, 4,4'-biphenylene diisocyanate, diphenylmethane-4,4'-diisocyanate, 3,3'-dimethoxy-4,4'-biphenyl diisocyanate, 3,3'-dimethyldiphenylmethane-4,4'-diisocyanate, isophorone diisocyanate and mixtures thereof.

The above-mentioned polycarbodiimides may be those produced with the molecular weight being controlled, for example, by terminating the polycondensation at a certain stage by the use of at least one monoisocyanate. Such a monoisocyanate used for terminal blocking of polycarbodiimide for its molecular weight control includes, for example, phenyl isocyanate, o-, m- or p-tolyl isocyanate, dimethylphenyl isocyanate, cyclohexyl isocyanate and methyl isocyanate.

As is easily inferred, there may be used, for terminal blocking of polycarbodiimide, a derivative of an isocyanate-terminated compound which can easily be produced by the reaction between about 1 mole of a compound having, at the terminal, —OH, —NH$_2$, —COOH, —SH or —NH-alkyl and 2 moles of an aromatic diisocyanate.

The catalyst which promotes the carbodiimidization of the organic polyisocyanate, includes various compounds. 1-phenyl-2-phospholene-1-oxide, 3-methyl-1-phenyl-2-phospholene-1-oxide, 1-ethyl-2-phospholene-1-oxide and 3-phospholene isomers thereof are preferred in view of the yield and other reasons.

Production of the above-mentioned polycarbodiimides is conducted using no solvent or in a non-reactive organic solvent. In the present invention, the thus-produced polycarbodiimides of varnish form or solid form (powder) can be used singly or in combination of two or more, as an example of the carbodiimide compound of the present invention. These polycarbodiimides may be crosslinked partially for increased bonding to the material.

In the present invention, there can also be used carbodiimide compounds other than those mentioned above, such as carbodiimide compounds having a polyoxyethylene chain in the molecule and consequently having hydrophilicity, described in Japanese Patent Application Kokai (laid-Open) Nos. 172718/1988 and 264128/1988.

The carbodiimide compound used in the present invention preferably has 2–100 carbodiimide groups in the molecule, regardless of the type of the compound. When the number of carbodiimide groups is less than 2, i.e. 1, the carbodiimide compound is deficient in immobilization of biologically active substance. When the number of carbodiimide groups is more than 100, the carbodiimide compound has no problem in immobilizability but, in some cases, has too high a viscosity or cannot be made into a solution, significantly reducing the handleability in loading it on the material.

The carbodiimide compound used in the present invention has a molecular weight of 1,000 or more, preferably 1,000–100,000.

Some of the above-mentioned polycarbodiimides produced from an organic polyisocyanate compound in the presence of a catalyst which promotes carbodiimidization of said isocyanate, have a molecular weight lower than 1,000. Such polycarbodiimides can be subjected to molecular weight control so as to have a molecular weight falling in the above range, by introducing, into both ends of the polycarbodiimide, a polyalkylene, a polyoxyalkylene, a polyurethane, a polyamide or the like via a urea bond or a urethane bond.

As mentioned above, the carbodiimide groups in the carbodiimide compound have high reactivity and react with substantially all the active hydrogen groups possessed by alcohols, amines, thiols, phenols, carboxylic acids, etc. The reaction with, for example, alcohol or amine proceeds as follows. (The reaction with carboxylic acid was shown previously).

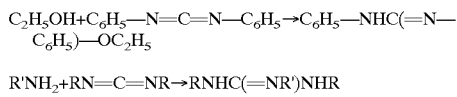

R'NH$_2$+RN=C=NR→RNHC(=NR')NHR

[Frederick Kurzer, K. Douraghi-Zadeh, Chemical Reviews, Vol.67, pp. 117–135 (1967) and Andrew Williams, Ibrahim T. Ibrahim, Chemical Reviews, Vol. 81, pp. 599–606 (1981)] In the present invention, such reactions allow for immobilization of an active substance.

The material of the present invention used for immobilization of active substance comprises the above-mentioned carrier and the above-mentioned carbodiimide compound supported thereon. The carbodiimide compound is supported on the material by utilizing the high adhesivity of the former to the latter. Herein, "supported" means that the carbodiimide compound is not eliminated from the material in water or other solvents.

The carbodiimide compound is supported on part or the whole area of the carrier, depending upon the application purpose of the resulting material. The form of the carbodiimide compound supported is typically a film.

The supporting of the carbodiimide compound on the carrier can be conducted by a known means such as spraying, immersion, brushing, stamping, vapor deposition, coating with a film coater, or the like.

The thus-obtained material of the present invention used for immobilization of active substance can immobilize various active substances owing to the reactivity of the carbodiimide compound contained in said material. Example of the active substances are biopolymers such as proteins, nucleic acids and the like. Specific examples of the active substances are enzymes, hormones, antibodies, antigens, haptenes, peptides, synthetic peptides, DNAs, synthetic DNAs, RNAs and synthetic RNAs.

Immobilization of an active substance by the present material can be conducted by contacting the two. The contact is preferably conducted in water or in a buffer so that the activity of the active substance can be maintained. The contact is preferably conducted at a temperature of 0–100° C. so that the activity of the active substance is not lost.

An active substance is immobilized on the material of the present invention very strongly and is not eliminated from the material even by the washing method (using a surfactant) widely used in the field of immunoassay. Therefore, an active substance immobilized on the present material has wide applications such as the industrial utilization of immobilized enzyme in the field of biochemistry or science, the immunological utilization of immobilized antibody or antigen, and the utilization of immobilized nucleic acid as diagnostic drug.

Incidentally, the mechanism by which an active substance is immobilized on the present material, is unclear yet, but the immobilization is presumed to take place by the two actions of chemical bonding and physical adsorption as disclosed in Frederick Kurzer, K. Douraghi-Zadeh, Chemical Reviews, Vol. 67, pp. 117–135 (1967).

The present invention is hereinafter described in mate detail by way of Examples.

Production of Carbodiimide Compound Solution 1

117.9 g of 4,4'-dicyclohexylmethane diisocyanate and 12.5 g of cyclohexyl isocyanate were reacted in the presence of 1.3 g of a carbodiimidization catalyst (3-methyl-1-phenyl-2-phospholene-1-oxide) in a nitrogen atmosphere at 180° C. for 4 days to obtain a carbodiimide compound (polymerization degree=10, number-average molecular weight=2,400) which was powdery at room temperature. 10 g of the polycarbodiimide compound was dispersed and dissolved in 100 ml of methanol to obtain a carbodiimide compound solution 1.

Production of Carbodiimide Compound Solution 2

19.9 g of isophorone diisocyanate and 2.0 g of n-butyl isocyanate were reacted in the presence of 0.2 g of a carbodiimidization catalyst (3-methyl-1-phenyl-2-phospholene-1-oxide) in a nitrogen atmosphere at 180° C. for 3 days to obtain a carbodiimide compound (polymerization degree=10, number-average molecular weight=1,900) which was powdery at room temperature. 10 g of the polycarbodiimide compound was dissolved in 100 ml of dichloromethane to obtain a carbodiimide compound solution 2.

Production of Carbodiimide Compound Solution 3

78.4 g of a 80:20 mixture of 2,4-tolylene diisocyanate and 2,6-tolylene diisocyanate and 11.9 g of phenylisocyanate were reacted in the presence of 0.9 g of a carbodiimidization catalyst (3-methyl-1-phenylphospholene-1-oxide) in 615 g of tetrachloroethylene in a nitrogen atmosphere at 75° C. for 24 hours to obtain a carbodiimide compound solution 3 (polymerization degree of polymer=10, number-average molecular weight of polymer=1,500).

Production of Carbodiimide Compound Solution 4

112.6 g of 4,4'-diphenylmethane diisocyanate and 11.9 g of phenyl isocyanate were reacted in the presence of 1.2 g of a carbodiimidization catalyst (3-methyl-1-phenylphospholene-1-oxide) in 922.7 g of tetrahydrofuran in a nitrogen atmosphere at 75° C. for 16 hours to obtain a carbodiimide compound solution 4 (polymerization degree of polymer=10, number-average molecular weight of polymer=2,300).

Production of Carbodiimide Compound Solution 5

700 g of m-tetramethylxylylene diisocyanate was reacted with 14 g of a carbodiimidization catalyst (3-ethyl-1-phenylphospholene-1-oxide) in a nitrogen atmosphere at 180° C. for 12 hours to obtain an isocyanate-terminated tetramethylxylylenecarbodiimide (polymerization degree=3). 74.6 g of the carbodiimide was reacted with 63.6 g of a poly(oxyethylene) monomethyl ether (polymerization degree=6) at 100° C. for 48 hours. To 10 g of the reaction product was slowly added 90 g of distilled water at 50$_0$C to obtain a carbodiimide compound solution 5 (number-average molecular weight of polymer=1,400).

Production of Carbodiimide Compound Solution 6

162 g of 4,4'-diphenylmethane diisocyanate was reacted with 0.33 g of a carbodiimidization catalyst (3-methyl-1-phenylphospholene-1-oxide) in 886 g of tetrahydrofuran in a nitrogen atmosphere under refluxing for 7 hours, to obtain a carbodiimide compound solution 6 (polymerization degree of polymer=60, number-average molecular weight of polymer=13,000, polymer concentration=15% by weight).

Production of Carbodiimide Compound Solution 7

700 g of m-tetramethylxylylene diisocyanate was reacted with 14 g of a carbodiimidization catalyst (3-methyl-1-phenylphospholene-1-oxide) in a nitrogen atmosphere at 180° C. for 18 hours to obtain an isocyanate-terminated tetramethylxylylenecarbodiimide (polymerization degree=4). 50.2 g of the carbodiimide was reacted with 8.9 g of 2-dimethylaminoethanol at 80° C. for 24 hours. The reaction product was reacted with 18.6 g of methyl p-toluenesulfonate for 1 hour. Thereto was slowly added 699.3 g of distilled water, to obtain a carbodiimide compound solution 7 (number-average molecular weight of polymer=1,600, polymer concentration=10% by weight).

Production of Carbodiimide Compound Solution 8

20 g of isophorone diisocyanate was reacted with 0.2 g of a carbodiimidization catalyst (3-methyl-1-phenyl-2-phospholene-1-oxide) in a nitrogen atmosphere at 180° C. for 18 hours to obtain an isocyanate-terminated isophoronecarbodiimide (polymerization degree=4). 7.56 g of the carbodiimide was reacted with 2.04 g of 3-dimethylamino-n-propylamine at 80° C. for 1 hour. The reaction product was reacted with 3.72 g of methyl p-toluenesulfonate for 1 hour. Thereto was slowly added 120 g of distilled water, to obtain a carbodiimide compound solution 8 (number-average molecular weight of polymer=1,400, polymer concentration=10% by weight).

Production of Carbodiimide Compound Solution 9

117.9 g of 4,4'-dicyclohexylmethane diisocyanate was reacted with 1.2 g of a carbodiimidization catalyst (3-methyl-1-phenyl-2-phospholene-1-oxide) in a nitrogen atmosphere at 180° C. for 8 hours to obtain an isocyanate-terminated dicyclohexylcarbodiimide (average polymerization degree=2.4). 7.85 g of the carbodiimide was reacted with 5.92 g of a poly(oxyethylene) monomethyl ether having a polymerization degree of about 6 at 100° C. for 48 hours. Thereto was slowly added 124 g of distilled water, to obtain a carbodiimide compound solution 9 (number-average molecular weight of polymer=1,300, polymer concentration=10% by weight).

Production of Carbodiimide Compound Solution 10

15 g of 4,4'-diphenylmethane diisocyanate was reacted with 0.1 g of a carbodiimidization catalyst (3-methyl-1-phenyl-2-phospholene-1-oxide) in 145 g of tetrahydrofuran in a nitrogen atmosphere at 75° C. for 8 hours to obtain an isocyanate-terminated diphenylmethanecarbodiimide (polymerization degree=5). The carbodiimide solution was reacted with 9.44 g of a poly (oxyethylene) monomethyl ether having a polymerization degree of about 10 at 75° C. for 48 hours to obtain a carbodiimide compound solution 10 (number-average molecular weight of polymer=2,100, polymer concentration=10% by weight).

Production of Carbodiimide Compound Solution 11

13.9 g of a 80:20 mixture of 2,4-tolylene diisocyanate and 2,6-tolylene diisocyanate was reacted with 0.1 g of a carbodiimidization catalyst (3-methyl-1-phenylphospholene-1-oxide) in 150 g of tetrahydrofuran in a nitrogen atmosphere at 75° C. for 8 hours to obtain an isocyanate-terminated tolylenecarbodiimide (polymerization degree=4). The carbodiimide solution was reacted with 1.62 g of sodium hydroxypropanesulfonate at 75° C. for 24 hours to obtain a carbodiimide compound solution 11 (number-average molecular weight of polymer=1,000, polymer concentration=10% by weight).

Production of Carbodiimide Compound Solution 12

24 g of 4,4'-diphenylmethane diisocyanate was reacted with 20 g of a polyethylene glycol having an average molecular weight of 400, in 440 g of tetrahydrofuran. Thereto was added 0.2 g of a carbodiimidization catalyst (3-methyl-1-phenylphospholene-1-oxide), and the mixture was subjected to a reaction in a nitrogen atmosphere at 75° C. for 48 hours to obtain a carbodiimide compound solution 12 (number-average molecular weight of polymer=5,300, polymer concentration=10% by weight)

Production of Carbodiimide Compound Solution 13

52.4 g of 4,4'-dicyclohexylmethanediisocyanate was reacted with 8.8 g of 1,4-diaminobutane in 620 g of tetrahydrofuran. Thereto was added 0.5 g of a carbodiimidization catalyst (3-methyl-1-phenylphospholene-1-oxide), and the mixture was subjected to a reaction in a nitrogen atmosphere at 75° C. for 48 hours to obtain a carbodiimide compound solution 13 (number-average molecular weight of polymer=3,700, polymer concentration=10% by weight).

EXAMPLE 1

(1) Immobilization of DNA Oligomer on Microplate 29 bases were selectively taken out from the multi-cloning site in the lac' Z zone of phage vector M13mp18. From the bases was synthesized a DNA having the following base sequence 1 by the use of a DNA synthesizer (Cyclone Plus DNA/RNA Synthesizer, a product of MILLIPORE Co.). Into the 5' terminal of the synthesized DNA was integrated biotinylated phosphoramidite (a product of MILLIPORE Co.) in order to selectively bond thereto a streptavidin-alkalinephosphatase conjugate protein. Incidentally, biotin phosphoramidite was indicated by B in the base sequence 1.

Base Sequence 1

5' BGA GGA TCC CCG GGT ACC GAG CTC GAA TTC 3'

0.1 ml of the carbodiimide compound solution 1 was placed in each of the five wells of a 96-well polystyrene-made microplate and incubated at 60° C. for 1 hour. The wells were thoroughly washed with ethanol, followed by drying at 60° C. for 30 minutes. 0.1 ml of a biotin-labeled DNA oligomer solution (an aqueous solution containing 10 pmol/ml of the above base sequence 1) was placed on each of the carbodiimide-coated five wells and non-coated five wells of the above microplate, and DNA immobilization was conducted at 37° C. for 2 hours. Then, each well was thoroughly washed with 0.3 ml of sterilized water five or six times, followed by drying at 60° C. for 30 minutes. The resulting microplate was stored in a cold dark place in a dry atmosphere.

(2) Detection

In order to suppress (or block) the non-specific adsorption of streptavidin-alkaline phosphatase conjugate on microplate wells, 0.2 ml of a 3% BSA solution [3% bovine serum albumin (BSA)/0.2 M NaCl/0.1 M Tris HCl, 0.05% Triton X-100] was placed in the DNA-incubated wells of the microplate, followed by incubation at 37° C. for 30 minutes. The BSA solution was removed by suction; then, 0.1 ml of a streptavidin-alkaline phosphatase conjugate solution [125 pg/ml streptavidin-alkaline phosphatase conjugate (a product of CLONTECH Co.)/0.2 M Tris HCl, 0.05% Triton X-100] was added, followed by incubation at room temperature for 30 minutes. Thereafter, washing was conducted with 0.3 ml of a washing solution 1 (0.2 M NaCl/0.1 M Tris HCl, 0.05% Triton X-100) three times (10 minutes each time) and with 0.3 ml of a washing solution 2 (0.1 M NaCl/0.1 M Tris HCl, pH 9.5/50 ml $MgCl_2$) one time. Next, there was added 0.1 ml of a substrate solution (1 mg p-nitrophenylphosphate disodium salt hexahydrate/0.1 M NaCl/0.1 M Tris HCl, pH 9.5/50 ml $MgCl_2$) to develop a color at room temperature for 2 hours. Then, the absorbance of the solution in each well was measured by the use of a spectrophotometer. The results are shown in Table 1.

EXAMPLE 2

(1) Immobilization of Streptavidin-Alkaline Phosphatase Conjugate on Microplate 0.1 ml of the carbodiimide compound solution 1 was placed in the five wells of a 96-well polystyrene-made microplate and incubated at 60° c. for 1 hour. The wells were thoroughly washed with methanol. Therein was placed 0.1 ml of a streptavidin-alkaline phosphatase conjugate solution [125 pg/ml streptavidin-alkaline phosphatase conjugate (a product of CLONTECH Co.)/0.2 M Tris HCl, 0.05% Triton X-100], followed by incubation at 37° C. for 30 minutes.

(2) Detection

Washing was conducted with 0.3 ml of a washing solution 1 (0.2 M NaCl/0.1 M Tris HCl, 0.05% Triton X-100) three times (10 minutes each time) and with 0.3 ml of a washing solution 2 (0.1M NaCl/0.1M Tris HCl, pH9.5/50ml $MgCl_2$) one time. Next, there was added 0.1 ml of a substrate solution (1 mg p-nitrophenylphosphate disodium salt hexahydrate/0.1 M NaCl/0.1 M Tris HCl, pH 9.5/50 ml $MgCl_2$) to develop a color at room temperature for 2 hours. The extent of color development in each well was evaluated visually. Also, the absorbance of the solution in each well was measured by the use of a spectrophotometer. The results are shown in Table 1.

EXAMPLE 3

A test was conducted in the same manner as in Example 1 except that the material was changed to a polystyrene-made microplate containing a carboxyl group at the surface (96F Plate Type C for SUMILON ELISA, a product of Sumitomo Bakelite Company Limited) and there were used the carbodiimide compound solutions 5, 7, 8 and 9. The results are shown in Table 1.

EXAMPLE 4

A test was conducted in the same manner as in Example 2 except that the material was changed to the same polystyrene-made microplate as used in Example 3 and there were used the carbodiimide compound solutions 5, 7, 8 and 9. The results are shown in Table 1.

EXAMPLE 5

Into a microplate coated with the carbodiimide compound solution 1, obtained in the same manner as in Example 1 was poured 0.2 ml of a solution containing 1 mg/ml of an ACTH peptide oligomer (a product of Peninsula Co.), obtained by diluting said ACTH peptide oligomer with 0.01 M HEPES (pH 7.0). After slight infiltration, the solution was discarded and the microplate surface was wiped lightly with a paper towel to remove the non-immobilized portion of ACTH peptide oligomer. This procedure was repeated three times. 0.2 ml of a blocking solution (0.01 M HEPES containing 10% of BSA, pH 7.0) was poured into each well to give rise to a reaction at 37° C. for 30 minutes. The solution in each well was discarded, and 0.2 ml of 0.01 M HEPES (pH 7.0) was poured into each well for washing. This procedure was repeated three times. Into each well was poured 0.1 ml of a solution obtained by diluting anti-ACTH-mouse-IgG (a solution of 1 mg/ml of said substance in 50% glycerose, a product of CYMBUS Bioscience Limited) 100-fold with 0.01 M HEPES (pH 7.0), to give rise to a reaction at room temperature for 30 minutes. The solution was discarded, and 0.2 ml of 0.01 M HEPES (pH7.0) was poured into each well for washing. This procedure was repeated three times. Into each well was poured 0.01 ml of a solution obtained by diluting alkaline phosphatase labeled anti-mouse-IgG-goat-IgG (a solution of 1 mg/ml of said substance in 50% glycerose, a product of Kirkegaaer & Perr Laboratory) 1,000-fold with 0.01 M HEPES (pH 7.0), to give rise to a reaction at room temperature for 30 minutes. The solution was discarded, and 0.2 ml of 0.01 M HEPES (pH 7.0) was poured into each well for washing. This procedure was repeated three times. Into each well was poured 0.01 ml of a substrate solution [50 mM borate buffer (pH 10. 0), 5 mM $MgCl_2$, 5 mM p-nitrophenylphosphate disodium salt], to give rise to a reaction at 30° C. for 1 hour. 0.2 ml of a 0.1 N aqueous sodiumhydroxide solution was added to terminate the reaction. The solution in each well was measured for absorbance at 405 nm by the use of a spectrophotometer. The above test was conducted for five wells. The results are shown in Table 1.

EXAMPLE 6

5 g of polystyrene beads [a poly(styrene-2% divinyl benzene), 200–400 mesh] were immersed for 30 minutes in 100 ml of a solution obtained by diluting the carbodiimide compound solution 1, 2, 3, 4, 6, 10, 11, 12 or 13, 10-fold with THF, and then dried at 60° C. for 3 hours to obtain carbodiimide compound-coated beads. 1 g of the carbodiimide compound-coated beads and 1 g of the non-coated beads (blank) were each immersed in the same biotin-labeled DNA oligomer (1 mg/10 ml) solution as used in Example 1, at 37° C. for 2 hours. Then, the beads were collected by filtration with a glass filter, washed with 500 ml of distilled water, and dried to obtain two kinds of DNA-immobilized beads. Each of the beads was subjected to the same blocking, streptavidin-alkaline phosphatase conjugate treatment and washing as in Example 1, and added to 3 ml of a substrate solution. Two hours later, each solution was measured for absorbance at 405 nm by the use of a spectrophotometer. The results are shown in Table 1.

EXAMPLE 7

1 g of the same carbodiimide compound-coated beads as used in Example 6 and 1 g of the same non-coated beads (blank) as used in Example 6 were each immersed in 3 ml of the same streptavidin-alkaline phosphatase conjugate solution as used in Example 2, at room temperature for 2 hours. Then, the beads were collected by filtration with a glass filter, washed with 500 ml of distilled water, and dried to obtain two kinds of streptavidin-alkaline phosphatase conjugate-immobilized beads. Each of the beads was subjected to the same washing as in Example 2 and added to 3 ml of a substrate solution. Two hours later, each solution was measured for absorbance at 405 nm by the use of a spectrophotometer. The results are shown in Table 1.

EXAMPLE 8

(1) Immobilization of DNA Oligomer on PET Film

A polyethylene terephthalate (PET) film was cut into rectangular pieces each of 1 cm×5 cm. Each PET piece was coated with 0.5 ml of the carbodiimide compound solution 1, 2, 3, 4, 6, 10, 11, 12 or 13 by the use of a spin coater and dried at 80° C. for 30 minutes to obtain carbodiimide compound-coated PET pieces. Each carbodiimide compound-coated PET piece and a non-coated PET piece (blank) were each stained in three dots each with 1 ml of a biotin-labeled DNA oligomer solution (an aqueous solution containing 100 pmol/ml of the base sequence 1), followed by immobilization at room temperature for 10 minutes.

(2) Detection

Detection was conducted by the use of GENE-TECT DETECTION SYSTEM of CLONTECH CO. in accordance with the detection protocol, as follows.

(a) Blocking

A DNA-immobilized PET piece was placed in a hybridization bag. Thereto was added 2 ml of a 3% BSA solution, followed by incubation at 37° C. for 30 minutes.

(b) Bonding of streptavidin-alkaline phosphatase conjugate

The BSA solution was removed by suction. Then, 1 ml of a streptavidin-alkaline phosphatase conjugate solution was added, followed by incubation at room temperature for 30 minutes.

(c) Washing

Washing was conducted with 2 ml of a washing solution 1 (0.2 M NaCl/0.1 M Tris HCl, 0.05% Triton X-100) three times (10 minutes each time).

(d) Buffer exchange

Washing was conducted with 2 ml of a washing solution 2 (0.1 M NaCl/0.1 M Tris HCl, pH 9.5/50 ml MgCl$_2$) one time.

(e) Color development

There were added 1 ml of a substrate solution [a washing solution 2 (0.1 M NaCl/0.1 M Tris HCl, pH 9.5/50 ml MgCl$_2$)], 3.2 ml of a BCIP solution (50 mg 5-bromo-4-chloro-3-indolyl phosphate/900 ml dimethyl formamide) and 1 ml of an NBT solution (50 mg Nitro Blue Tetrazolium/1.8 ml 70% methanol) to give rise to color development in a dark place of room temperature for 3 hours.

(f) Results

The results are shown in Table 2.

EXAMPLE 9

(1) Immobilization of Streptavidin-Alkaline Phosphatase

The same carbodiimide compound-coated PET piece and non-coated PET piece (blank) as used in Example 8 were each stained in three dots with a streptavidin-alkaline phosphatase conjugate solution (0.2 M Tris HCl, 0.05% Triton X-100, a product of CLONTECH Co.), followed by immobilization at room temperature for 10 minutes.

(2) Detection (a) Washing

Washing was conducted with 2 ml of a washing solution 1 (0.2 M NaCl/0.1 M Tris HCl, 0.05% Triton X-100) three times (10 minutes each time).

(b) Buffer exchange

Washing was conducted with 2 ml of a washing solution 2 (0.1 M NaCl/0.1 M Tris HCl, pH 9.5/50 ml MgCl$_2$) one time.

(c) Color development

There were added 1 ml of a substrate solution [a washing solution 2 (0.1 M NaCl/0.1 M Tris HCl, pH 9.5/50 ml MgCl$_2$)], 3.2 µl of a BCIP solution (50 mg 5-bromo-4-chloro-3-indolyl phosphate/900 ml dimethyl formamide) and 1 ml of an NBT solution (50 mg Nitro Blue Tetrazolium/1.8 ml 70% methanol) to give rise to color development in a dark place of room temperature for 3 hours.

(d) Results

The results are shown in Table 2.

EXAMPLE 10

(1) Immobilization of DNA Oligomer on Glass Plate

The carbodiimide compound solution 1, 2, 3, 4, 6, 10, 11, 12 or 13 was coated on a glass plate in the same manner as in Example 8, and a DNA was immobilized thereon in the same manner as in Example 8.

(2) Detection

The immobilized DNA was detected in the same manner as in Example 8. The results are shown in Table 2.

EXAMPLE 11

(1) Immobilization of Streptavidin-Alkaline Phosphatase Conjugate on Glass Plate The 10% carbodiimide compound solution 1, 2, 3, 4, 6, 10, 11, 12 or 13 was coated on a glass plate in the same manner as in Example 8, and streptavidin-alkaline phosphatase conjugate was immobilized thereon in the same manner as in Example 9.

(2) Detection

The immobilized streptavidin-alkaline phosphatase conjugate was detected in the same manner as in Example 9. The results are shown in Table 2.

EXAMPLE 12

(1) Immobilization of DNA Oligomer on Copper Plate

The 10% carbodiimide compound solution 1, 2, 3, 4, 6, 10, 11, 12 or 13 was coated on a copper plate in the same manner as in Example 8, and a DNA was immobilized thereon in the same manner as in Example 8.

(2) Detection

The immobilized DNA was detected in the same manner as in Example 8. The results are shown in Table 2.

EXAMPLE 13

(1) Immobilization of Streptavidin-Alkaline Phosphatase Conjugate on Copper Plate The 10% carbodiimide compound solution 1, 2, 3, 4, 6, 10, 11, 12 or 13 was coated on a copper plate in the same manner as in Example 8, and streptavidin-alkaline phosphatase conjugate was immobilized thereon in the same manner as in Example 9.

(2) Detection

The immobilized streptavidin-alkaline phosphatase conjugate was detected in the same manner as in Example 9. The results are shown in Table 2.

In each of Examples 8–13, the thickness of the carbodiimide compound coated was measured and found to be 0.5–1 µm. Also, the surface of the carbodiimide compound film was measured for infrared absorption, which showed a carbodiimide-based absorption at around 2,100cm$^{-1}$. Thus, the substance coated on the material was confirmed to be a carbodiimide compound.

EXAMPLE 14

A filter paper (No. 42, a product of Whatman Co.) was immersed in a solution (obtained by diluting the carbodiimide compound solution 1, 2, 3, 4, 6, 10, 11, 12or 13 with THF 20-fold) for 10 minutes and dried at 60° C. for 30 minutes to obtain a carbodiimide compound-coated filter paper. On this paper was immobilized a DNA in the same manner as in Example 3. Then, the immobilized DNA was detected, in the same manner as in Example 3. The results are shown in Table 2.

EXAMPLE 15

On the same carbodiimide compound-coated filter paper as used in Example 14 was immobilized streptavidin-alkaline phosphatase conjugate in the same manner as in Example 4. Then, the conjugate was detected in the same manner as in Example 4. The results are shown in Table 2.

EXAMPLE 16

A microfilter (FR Type, pore diameter=0.7 µm, a product of Fuji Photo Film Co., Ltd.) was immersed for 10 seconds in a solution (obtained by diluting the carbodiimide compound solution 1, 2, 3, 4, 6, 10, 11, 12 or 13 with THF 20-fold), and dried at 60° C. for 30 minutes to obtain a carbodiimide compound-coated blotting membrane. This membrane was subjected to southern hybridization according to Molecular Cloning 9.31–9.51 (Molecular Cloning, a laboratory manual second edition, Cold Spring Harbor Laboratory Press, 1989).

1 µg of DNA molecular weight markers (DNA MW Standard Markers, λ-Hind III Digest, a product of Takara Shuzo Co., Ltd.) was subjected to fractionation by 1% agarose gel electrophoresis. The resulting fragment was capillary-transferred onto the above-obtained membrane. Then, 0.5 µg of a biotinylated probe, which was produced from λ-DNA (bacteriophage λcI 857 Sam7 NAs, a product of Takara Shuzo Co., Ltd.) by the use of Random Primer Biotinylation Kit (a product of STRATAGENE Co.), was hybridized with above-mentioned fragment of DNA molecular weight markers. Incidentally, after the transfer, the UV application, which is generally conducted to a nitrocellulose membrane or a nylon membrane, was not conducted to the above membrane coated with the carbodiimide compound solution, and hybridization was effected without conducting the UV application. Detection was conducted by the use of Flash (registered trademark) Detection System (a product of STRATAGENE Co.). As a result, the same signal of the fragment obtained by agarose electrophoresis, as shown in electrophoresis pattern, was detected on an X-ray film.

COMPARATIVE EXAMPLES 1–15

The same procedures as in Examples 1–15 were repeated except that no carbodiimide compound was used. The results are shown in the "non-coated" columns of Tables 1 and 2.

COMPARATIVE EXAMPLE 17

Detection of DNA by Conventional Method Immobilization of Modified DNA by Conventional Chemical Bonding Using Glutaraldehyde 29 bases were selectively taken out from the multi-cloning site in the lac' Z zone of phage vector M13mp18. From the bases was synthesized a DNA having the following base sequence 2 by the use of a DNA synthesizer (Cyclone Plus DNA/RNA Synthesizer, a product of MILLIPORE Co.). Into the second position from the 3' terminal, of the sequence of the synthesized DNA was integrated biotinylated phosphoramidite (a product of MILLIPORE Co.) in order to selectively bond thereto a streptavidin-alkaline phosphatase conjugate protein; and an amino linker (a product of MILLIPORE Co.) was integrated into the 5' terminal of the DNA. Incidentally, in the base sequence 2, biotin phosphoramidite was indicated by B and the amino linker was indicated by $H_2N-$.

Base Sequence 2

5' $H_2N$-GAG GAT CCC CGG GTA CCG AGC TCG AAT TBC 3'

0.1 ml of a 2% glutaraldehyde (electron microscope grade) solution [2% glutaraldehyde/PBS buffer solution (pH 7.4)] was placed in each of the 5 wells of a polystyrene-made microplate containing an amino group at the surface (96F Plate Type A for SUMILON ELISA, a product of Sumitomo Bakelite Company Limited), and allowed to stand at room temperature for 2 hours. Washing with water was conducted two times. Into each of the 5 wells treated with 2% glutaraldehyde was placed 0.1 ml of an amino linker-modified biotin-labeled DNA oligomer solution (an aqueous solution containing 10 pmol/ml of the base sequence 2), and DNA immobilization was conducted at 37° C. for 2 hours. Detection was conducted in the same manner as in Example 1. The results are shown in Table 1.

TABLE 1

| Examples & Comparative Examples | Carbodiimide Compound Solution | Base Material | Immobilized Substance | Absorbance Coated | Absorbance Non-Coated |
|---|---|---|---|---|---|
| 1 | 1 | Polystyrene-made microplate | DNA | 44.1 ± 0.7 | 0.49 ± 0.04 |
| 2 | 1 | Polystyrene-made microplate | Enzyme-antibody | 10.9*[1] ± 0.9 | 0.67*[2] ± 0.08 |
| 3 | 5,7,8,9 | Polystyrene-made microplate | DNA | 30.7 ± 0.5 | 0.49 ± 0.02 |
| 4 | 5,7,8,9 | Polystyrene-made microplate | Enzyme-antibody | 10.6 ± 0.5 | 0.62 ± 0.07 |
| 5 | 1 | Polystyrene-made microplate | Peptide (hormone) | 5.07 ± 0.03 | 0.97 ± 0.03 |
| 6 | 1,2,3,4,6, 10,11,12,13 | Polystyrene-made beads | DNA | 100 | 1.5 |
| 7 | 1,2,3,4,6, 10,11,12,13 | Polystyrene-made beads | Enzyme-antibody | 55.5 | 0.5 |
| 17 | | Polystyrene-made microplate | DNA | | 2.61 ± 1.36 |

*[1]Yellow
*[2]Colorless

TABLE 2

| Examples & Comparative Examples | Carbodiimide Compound Solution | Base Material | Immobilized Substance | Color Development Coated | Color Development Non-Coated |
|---|---|---|---|---|---|
| 8 | 1,2,3,4,6, 10,11,12,13 | PET film | DNA | ◯ | X |
| 9 | 1,2,3,4,6, 10,11,12,13 | PET film | Enzyme-antibody | ◯ | X |
| 10 | 1,2,3,4,6, 10,11,12,13 | Glass plate | DNA | ◯ | X |
| 11 | 1,2,3,4,6, 10,11,12,13 | Glass plate | Enzyme-antibody | ◯ | X |
| 12 | 1,2,3,4,6, | Copper plate | DNA | ◯ | X |

TABLE 2-continued

| Examples & Comparative Examples | Carbodiimide Compound Solution | Base Material | Immobilized Substance | Color Development | |
|---|---|---|---|---|---|
| | | | | Coated | Non-Coated |
| 13 | 10,11,12,13 1,2,3,4,6, 10,11,12,13 | Copper plate | Enzyme-antibody | ◯ | X |
| 14 | 1,2,3,4,6, 10,11,12,13 | Filter paper | DNA | ◯ | X |
| 15 | 1,2,3,4,6, 10,11,12,13 | Filter paper | Enzyme-antibody | ◯ | X |

◯: A developed color was detected.
X: No developed color was detected.

As is clear from the results of Tables 1 and 2, the present invention can provide a material which can immobilize a biologically active substance easily and which is easy to handle, and a process for easily immobilizing a biologically active substance using said material.

What is claimed is:

1. An immobilized biologically active substance selected from the group consisting of an antibody, an antigen, a DNA, a synthetic DNA, an RNA and a synthetic RNA, which is reactive with a carbodiimide group, comprising said biologically active substance immobilized on a material comprising a carrier selected from the group consisting of a plastic, an inorganic polymer, a metal, a natural polymer and a ceramic, and a carbodiimide group-containing polymer supported on the carrier, said polymer containing 2 to 100 carbodiimide groups per molecule and having a molecular weight of 1,000–100,000 and being produced by carbodiimidization of an organic polyisocyanate selected from the group consisting of 2,4-tolylene diisocyanate, 2,6-tolylene diisocyanate, 4,4'-dicyclohexylmethane diisocyanate, 4,4',4"-triphenylmethylene triisocyanate, xylene diisocyanate, m-tetramethylxylylene diisocyanate, hexamethylene-1,6-diisocyanate, lysine diisocyanate, hydrogenated methylene diphenyl diisocyanate, m-phenyl diisocyanate, naphthylene-1,5-diisocyanate, 4,4'-biphenylene diisocyanate, diphenylmethane-4,4'-diisocyanate, 3,3'dimethoxy-4,4'-biphenyl diisocyanate, 3,3'-dimethyldiphenylmethane-4,4'-diisocyanate, isophorone diisocyanate and mixtures thereof.

2. An immobilized biologically active substance according to claim 1, wherein the carbodiimide group-containing polymer is supported on a part or the whole area of the carrier.

3. An immobilized biologically active substance according to claim 1, wherein the carbodiimide group-containing polymer is supported on the carrier in the form of a film.

4. A method for immobilization of a biologically active substance, which comprises contacting a biologically active substance selected from the group consisting of an antibody, an antigen, a DNA, a synthetic DNA, an RNA and a synthetic RNA, which is reactive with a carbodiimide group, with a material for immobilization of said substance, said material comprising a carrier selected from the group consisting of a plastic, an inorganic polymer, a metal, a natural polymer and a ceramic, and a carbodiimide group-containing polymer supported thereon, said polymer containing 2 to 100 carbodiimide groups per molecule and having a molecular weight of 1,000–100,000, and being produced by carbodiimidization of an organic polyisocyanate selected from the group consisting of 2,4-tolylene diisocyanate, 2,6-tolylene diisocyanate, 4,4'-dicyclohexylmethane diisocyanate, 4,4',4"-triphenylmethylene triisocyanate, xylene diisocyanate, m-tetramethylxylylene diisocyanate, hexamethylene-1,6-diisocyanate, lysine diisocyanate, hydrogenated methylene diphenyl diisocyanate, m-phenyl diisocyanate, naphthylene-1,5-diisocyanate, 4,4'-biphenylene diisocyanate, diphenylmethane-4,4'-diisocyanate, 3,3'-dimethoxy-4,4'-biphenyl diisocyanate, 3,3'-dimethyldiphenylmethane-4,4'-diisocyanate, isophorone diisocyanate and mixtures thereof.

5. A method according to claim 4, wherein the carbodiimide group-containing polymer is supported on a part or the whole area of the carrier.

6. A method according to claim 4, wherein the carbodiimide group-containing polymer is supported on the carrier in the form of a film.

* * * * *